US010473561B2

(12) United States Patent
Pellerin (10) Patent No.: US 10,473,561 B2
(45) Date of Patent: Nov. 12, 2019

(54) METHOD OF SAMPLING A CRYOGENIC LIQUID

(71) Applicant: Air Liquide Canada, Inc., Varennes (CA)

(72) Inventor: Joseph Philippe Pellerin, Montreal (CA)

(73) Assignee: Air Liquide Canada, Inc., Montreal, QC (CA)

( * ) Notice: Subject to any disclaimer, the term of this patent is extended or adjusted under 35 U.S.C. 154(b) by 135 days.

(21) Appl. No.: 15/823,785

(22) Filed: Nov. 28, 2017

(65) Prior Publication Data

US 2019/0162633 A1 May 30, 2019

(51) Int. Cl.
| | | |
|---|---|---|
| *G01N 1/10* | (2006.01) | |
| *G01N 1/20* | (2006.01) | |
| *F17C 13/00* | (2006.01) | |
| *F17C 9/02* | (2006.01) | |
| *G01N 1/22* | (2006.01) | |

(52) U.S. Cl.
CPC ............... *G01N 1/10* (2013.01); *F17C 9/02* (2013.01); *F17C 13/00* (2013.01); *G01N 1/20* (2013.01); *G01N 1/2226* (2013.01); *G01N 1/2035* (2013.01); *G01N 2001/205* (2013.01); *G01N 2001/2238* (2013.01)

(58) Field of Classification Search
CPC .......... G01N 1/10; G01N 1/20; G01N 1/2035; G01N 2001/205; F17C 13/00; F17C 13/02
See application file for complete search history.

(56) References Cited

U.S. PATENT DOCUMENTS

| | | | | | |
|---|---|---|---|---|---|
| 3,123,982 | A | * | 3/1964 | Brown et al. | F17C 13/02 141/4 |
| 3,357,256 | A | * | 12/1967 | Burch | F17C 13/00 73/863.11 |
| 4,715,187 | A | * | 12/1987 | Stearns | F17C 9/00 62/50.1 |
| 4,991,449 | A | * | 2/1991 | Dieguez | G01N 1/10 73/863.11 |
| 5,161,381 | A | * | 11/1992 | Victor | G01N 1/22 62/50.1 |
| 6,212,948 | B1 | * | 4/2001 | Ekdahl | E21B 43/34 166/250.16 |
| 2002/0170364 | A1 | * | 11/2002 | Gerard | F17C 13/12 73/863.86 |

(Continued)

*Primary Examiner* — Herbert K Roberts
(74) *Attorney, Agent, or Firm* — Elwood L. Haynes (57) ABSTRACT

One embodiment of the method includes: closing both the inlet valve and the outlet valve, connecting a cryogenic liquid source to the cryogenic liquid inlet conduit, and introducing cryogenic liquid into the cryogenic liquid inlet conduit; opening both the inlet valve and outlet valve, thereby introducing cryogenic liquid into the sampler vessel inner volume, the cryogenic liquid has a free surface; closing both the inlet valve and the outlet valve after cryogenic liquid flows from the purge tube; disconnecting the cryogenic liquid source from the cryogenic liquid inlet conduit; opening the inlet valve, thereby allowing cryogenic liquid to flow from the cryogenic liquid inlet conduit; and closing the inlet valve after the free surface in the sampler vessel inner volume drops below the top of the first cryogenic liquid level, and the cryogenic liquid flow stops.

18 Claims, 9 Drawing Sheets

(56) References Cited

U.S. PATENT DOCUMENTS

2006/0218941 A1* 10/2006 Drube .................. F17C 5/02
  62/50.2
2012/0073806 A1* 3/2012 Barrows ................ E21B 43/34
  166/264

* cited by examiner

Figure 3b
Filling

Figure 3a
Attachment

Figure 3d
Filling

Figure 3c
Filling

Figure 3f
Fluid Level Adjustment

Figure 3e
Fluid Level Adjustment

METHOD OF SAMPLING A CRYOGENIC LIQUID

BACKGROUND

Cryogenic liquids, for example, liquid nitrogen, oxygen and argon are employed in a number of environments and have a number of industrial and commercial applications in which the user demands high purity which necessitates accurate information as to the analytical content of trace or low level amounts of contaminating gases. Analysis is carried out on a gaseous sample of the cryogenic liquid which typically involves the use of a flash vaporizer.

A particular difficulty arises in obtaining a gas sample which has the same molar concentration of trace contaminants as the cryogenic liquid being sampled. Thus, for example, liquid nitrogen may typically contain trace amounts of one or more of helium, hydrogen, neon, argon, oxygen, methane, carbon monoxide, carbon dioxide and water. When the temperature of the liquid nitrogen is raised, vaporization or evaporation of the nitrogen and the different contaminating gases takes place at different temperatures and thus at different points in time.

Thus any hydrogen, helium and neon tends to vaporize before the nitrogen and any argon, oxygen, methane, carbon monoxide, carbon dioxide and water tends to vaporize after the nitrogen. In this way fractionation of the sample occurs and the analytical composition of the gas sample continuously obtained varies continuously and does not accurately represent the analytical composition of the cryogenic liquid.

Available samplers do not fully address the problem of fractionation of the cryogenic liquid during volatilization whereby the gas sample is not a true sample of the liquid. In many cases the resulting discrepancies are not serious, however, many users are demanding liquids of ever greater purity so that it becomes increasingly necessary to be able to detect low level contaminants.

Therefore, a need exists in the industry for a cryogenic liquid sampler that satisfies these requirements.

SUMMARY

One embodiment of a method of taking a cryogenic liquid is provided. The methods uses a sampler including an inner volume, and an inner wall, a cryogenic liquid inlet conduit in fluid connection with an inlet valve, a weir tube in fluid connection with the inlet valve, the weir tube has a top plug and at least one weir hole, the weir tube extends into the inner volume, a first cryogenic liquid level is the distance along the weir tube between the inner wall and the at least one weir hole, a cryogenic liquid outlet conduit in fluid connection with the inner volume and in fluid connection with an outlet valve, and a purge tube in fluid connection with the outlet valve.

One embodiment of the method includes: closing both the inlet valve and the outlet valve, connecting a cryogenic liquid source to the cryogenic liquid inlet conduit, and introducing cryogenic liquid into the cryogenic liquid inlet conduit; opening both the inlet valve and outlet valve, thereby introducing cryogenic liquid into the sampler vessel inner volume, wherein the cryogenic liquid has a free surface; closing both the inlet valve and the outlet valve after cryogenic liquid flows from the purge tube; disconnecting the cryogenic liquid source from the cryogenic liquid inlet conduit; opening the inlet valve, thereby allowing cryogenic liquid to flow from the cryogenic liquid inlet conduit; and closing the inlet valve after the free surface in the sampler vessel inner volume drops below the top of the first cryogenic liquid level, and the cryogenic liquid flow stops.

A method for sampling a cryogenic liquid while maintaining the constituent composition is provided. This method uses a cryogenic liquid sampler with an inner volume and a weir tube extending a predetermined distance into the inner volume. The method includes filling the cryogenic liquid sampler with a cryogenic liquid with a constituent composition, removing a stream of cryogenic liquid from the sampler through the weir tube, thereby creating a lower pressure region of vapor above the cryogenic liquid with the constituent composition, and sealing the cryogenic liquid sampler once the stream of cryogenic liquid stops, thereby retaining a residual portion of cryogenic liquid with the constituent composition.

BRIEF DESCRIPTION OF THE FIGURES

For a further understanding of the nature and objects for the present invention, reference should be made to the following detailed description, taken in conjunction with the accompanying drawings, in which like elements are given the same or analogous reference numbers and wherein.

ELEMENT NUMBERS

100=cryogenic liquid sampler
101=cryogenic liquid inlet conduit
102=inlet valve
103=weir tube
104=weir tube top plug
105=weir hole (in weir tube)
106=minimum fill point (of weir hole)
107=sampler vessel
108=inner volume (of sampler vessel)
109=inner wall (of sampler vessel)
110=cryogenic liquid outlet conduit
111=outlet valve
112=purge tube
113=cryogenic liquid
114=cryogenic vapor
115=free surface of cryogenic liquid
116=cryogenic liquid level (at free surface of cryogenic liquid)
117=cryogenic liquid source
118=pressure indicator

DESCRIPTION OF PREFERRED EMBODIMENTS

Illustrative embodiments of the invention are described below. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

As used herein, the term "cryogenic" is defined in its normal meaning as concerning any liquid at a temperature below −73° C. This definition of course includes, but is not limited to, other liquefied gases including, but not necessarily limited to, oxygen, nitrogen, hydrogen, hydrocarbon gases (e.g. methane and the like) at temperatures of approximately −162 C.

As used herein, the term "free surface" is defined as meaning the surface of a fluid that is subject to zero parallel shear stress, such as the boundary between two homogeneous fluids, in this case, the boundary between a cryogenic liquid and a cryogenic vapor. As used herein, the "free surface" demarks the upper boundary of the cryogenic liquid, in a direction that is perpendicular to the effects of gravity.

The cryogenic liquid source 117, may be any device, method, or operation that produces, stores, or processes any liquid at cryogenic temperatures. In one embodiment, cryogenic liquid source 117 may be a product stream generated by a cryogenic air separation unit (not shown). Often, the purity of the cryogenic liquid will need to be checked or verified. Cryogenic liquid source 117, which is presumed to be homogeneous, has a constituent composition, which is defined as the in-situ ratios of the various components and contaminants. It is critical, when taking a sample of this cryogenic liquid, to maintain the constituent composition.

Turning to FIGS. 1a, 1b, 2a, 2b, and 5, cryogenic liquid sampler 100 is provided. Cryogenic liquid sampler 100 includes cryogenic liquid inlet conduit 101, cryogenic liquid outlet conduit 110, inner wall 109, and an inner volume 108. Cryogenic liquid sampler 100 may be made of any material that is compatible with the cryogenic liquid to be sampled, the cryogenic temperatures to be encountered, and the elevated pressures that will be present during transport. Cryogenic liquid sampler 100 may be made of stainless steel, preferably 304 stainless steel. Cryogenic liquid sampler 100 may also include pressure indicator 118.

Figure 1A:
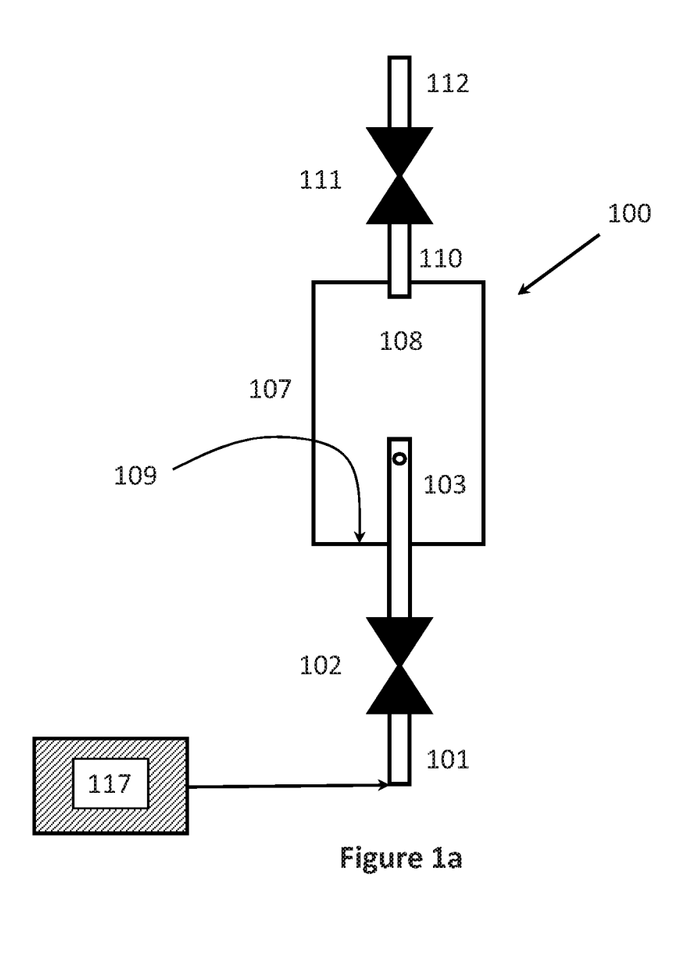
FIG. 1a is a schematic representation of one embodiment of the present invention.
Figure 1B:
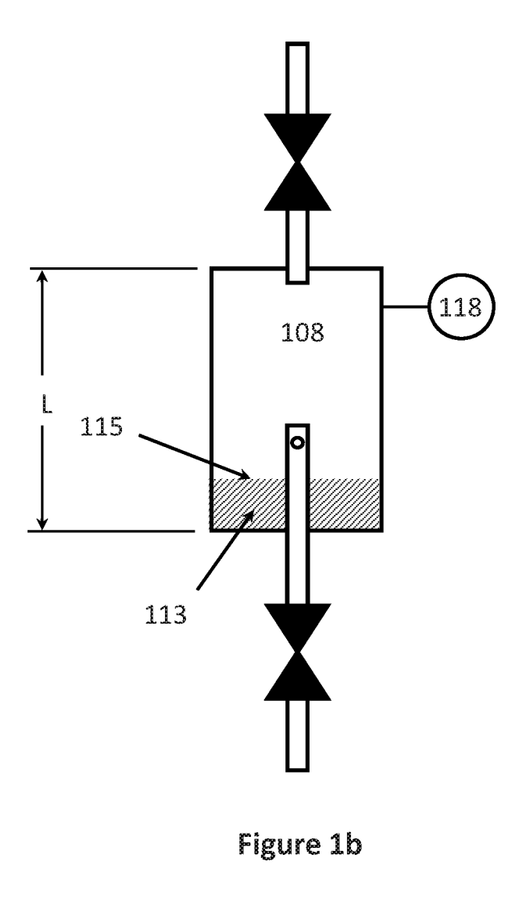
FIG. 1b is a schematic representation of one embodiment of the present invention.
Figure 2A:
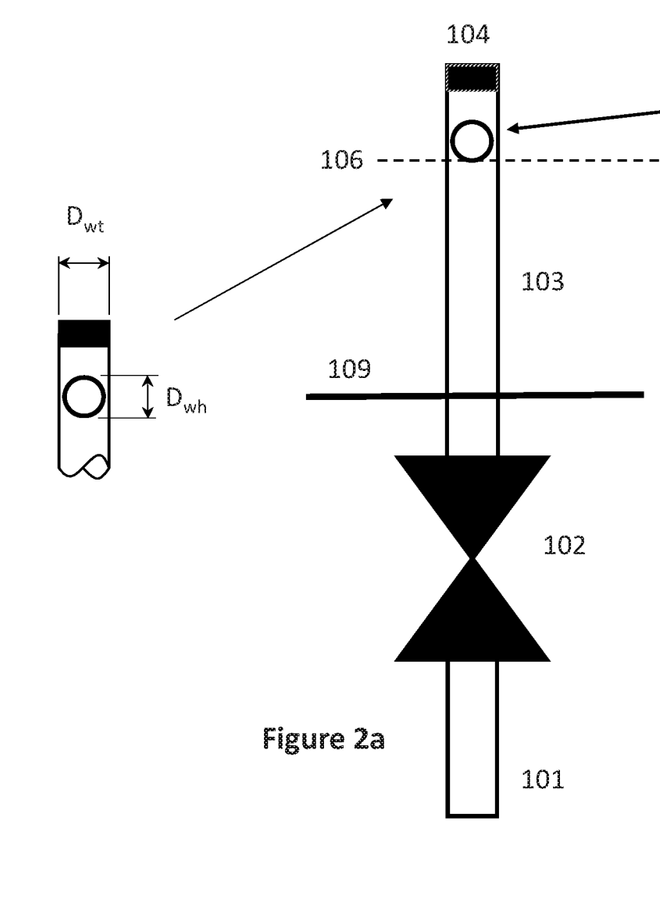
FIG. 2a is a schematic representation of the weir tube with a circular weir hole, in accordance with one embodiment of the present invention.
Figure 2B:
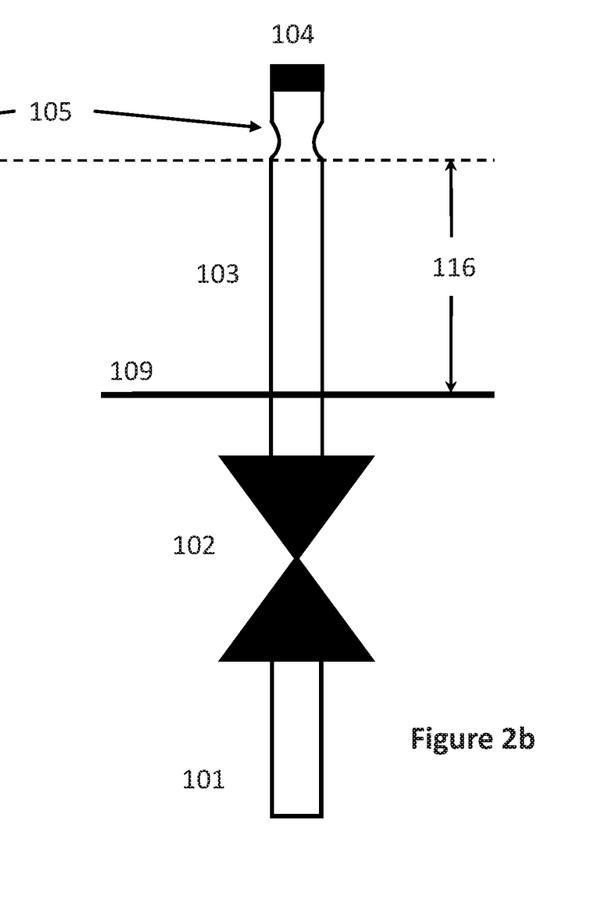
FIG. 2b is a schematic representation of the weir tube with a circular weir hole, in accordance with one embodiment of the present invention.
Figure 2C:
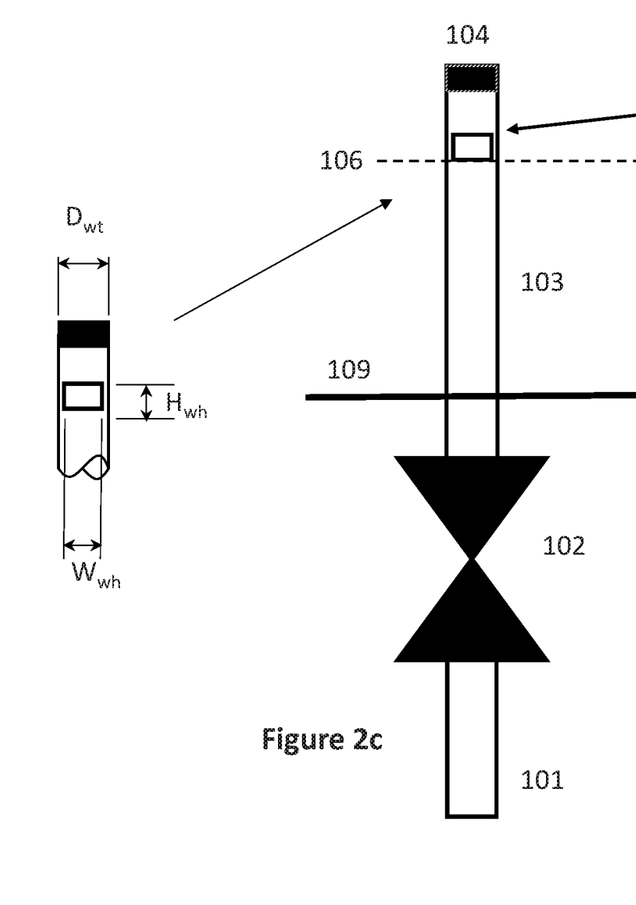
FIG. 2c is a schematic representations of the weir tube with a rectangular weir hole, in accordance with one embodiment of the present invention.
Figure 2D:
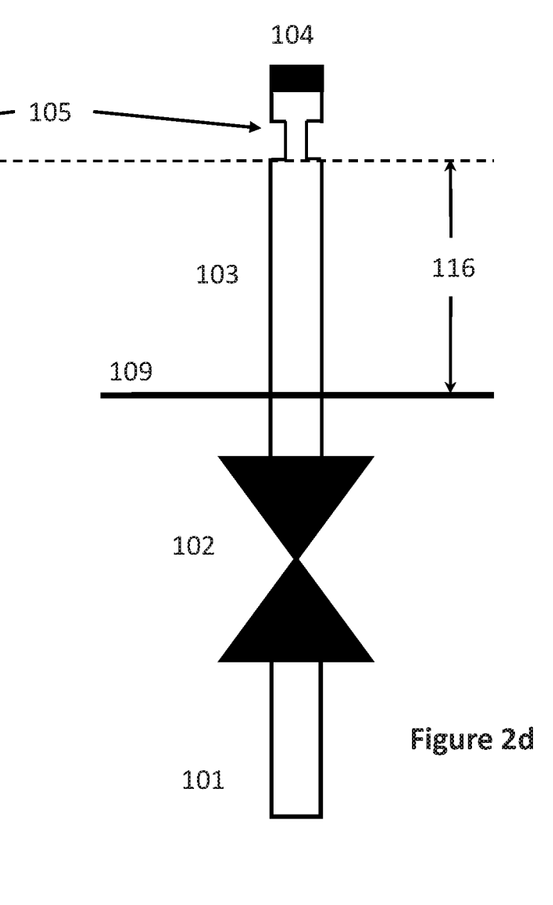
FIG. 2d is a schematic representations of the weir tube with a rectangular weir hole, in accordance with one embodiment of the present invention.

Cryogenic liquid inlet conduit 101 includes inlet valve 102 and weir tube 103. Weir tube 103 includes weir tube top plug 104 and at least one weir hole 105. As illustrated in FIGS. 2a and 2b, weir hole 105 may be circular, with a diameter of $D_{wh}$. As illustrated in FIGS. 2c and 2d, weir hole 105 may be rectangular, with a width of $W_{wh}$ and a height of $H_{wh}$. Weir tube 103 extends into inner volume 108 of sampler vessel 107. The bottom of weir hole 105 is the minimum fill point 106 and is the point along the perimeter of weir hole 105 that is closest to inner wall 109, being situated a predetermined distance 116 from inner wall 109. Cryogenic liquid outlet conduit 110 includes outlet valve 111 and purge tube 112. As will be discussed below, the predetermined distance 116 will ultimately determine the liquid sample volume.

Figure 3A:
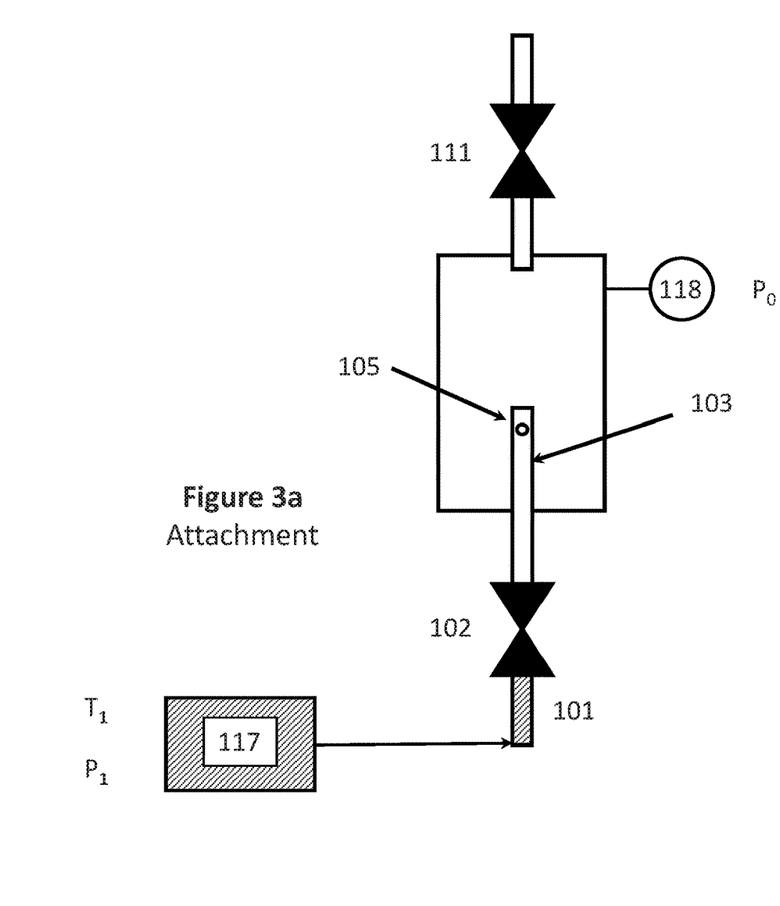
FIG. 3a is a schematic representation of the attachment phase, in accordance with one embodiment of the present invention.

Now turning to FIGS. 3a-3h, a method of taking a sample of a cryogenic liquid is provided. What may be referred to as "the attachment phase, is indicated in FIG. 3a. In the attachment phase, cryogenic liquid source 117 is attached to cryogenic liquid inlet conduit 101. At this time, the inner volume 108 of sampler vessel 107 has a pressure of P0. P0 may be approximately atmospheric pressure. Cryogenic liquid source 117 has a delivery pressure P1. P1 may be greater than P0.

Figure 3B:
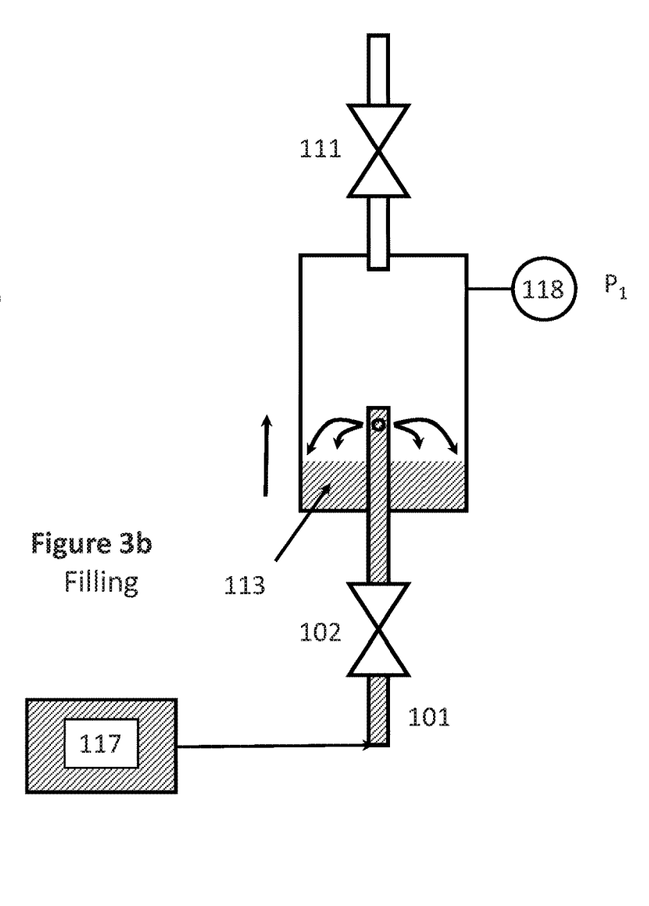
FIG. 3b is a schematic representation of the filling phase, in accordance with one embodiment of the present invention.
Figure 3C:
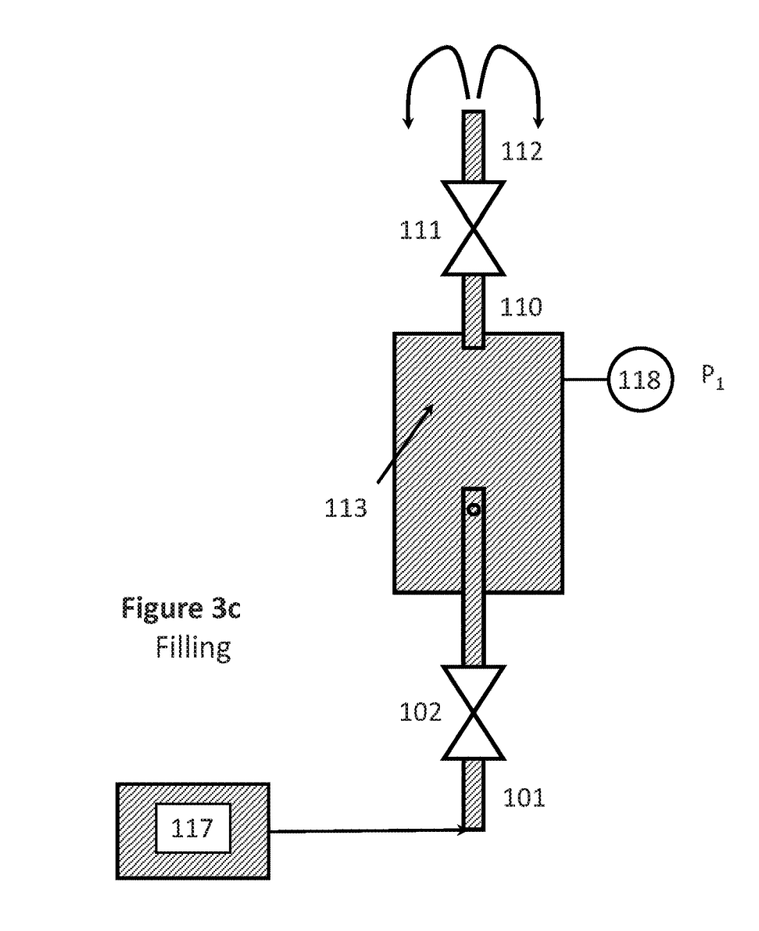
FIG. 3c is a schematic representation of the filling phase, in accordance with one embodiment of the present invention.
Figure 3D:
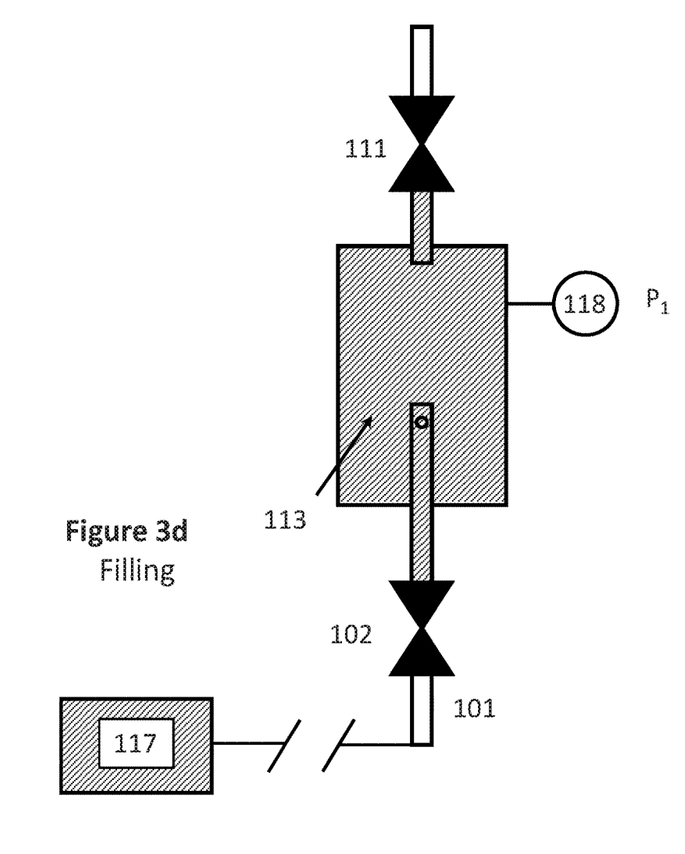
FIG. 3d is a schematic representation of the filling phase, in accordance with one embodiment of the present invention.

What may be referred to as the "filling phase" is indicated in FIGS. 3b-3d. When it is desired to actually take the cryogenic liquid sample, as indicated in FIG. 3b, inlet valve 102 and outlet valve 111 are opened, allowing cryogenic liquid 113 to flow through weir tube 103 and begin filling inner volume 108 of sampler vessel 107.

As indicated in FIG. 3c, once cryogenic liquid 113 completely occupies inner volume 108, it then flows out cryogenic liquid outlet conduit 110, outlet valve 111, and through purge tube 112, where it is vented or otherwise properly disposed of (not shown). At this time, it may be desirable to partially close outlet valve 111 in order to reduce the flowrate of cryogenic liquid 113 out of purge tube 112. Once a steady stream of cryogenic liquid 113 is flowing out of purge tube 112, and no more residual air is present in inner volume 108, inlet valve 102 and outlet valve 111 are simultaneously closed, as indicated in FIG. 3d. Cryogenic liquid source 117 is then detached from cryogenic liquid inlet conduit 101. At this time, the cryogenic liquid that fills inner volume 108 is at a pressure of approximately P1.

Figure 3E:
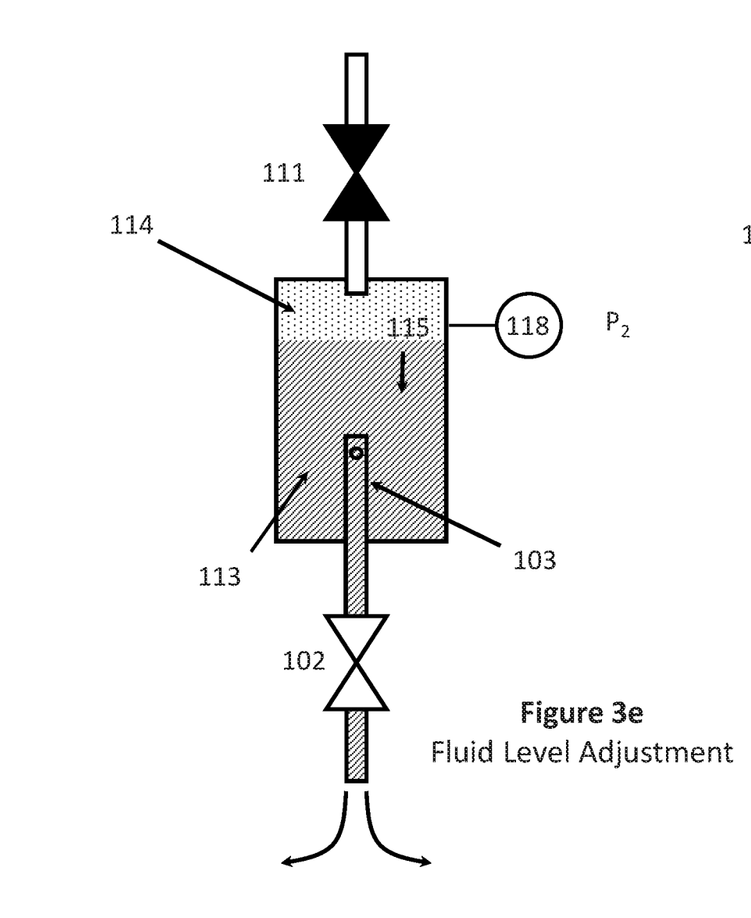
FIG. 3e is a schematic representation of the fluid level adjustment phase, in accordance with one embodiment of the present invention.
Figure 3F:
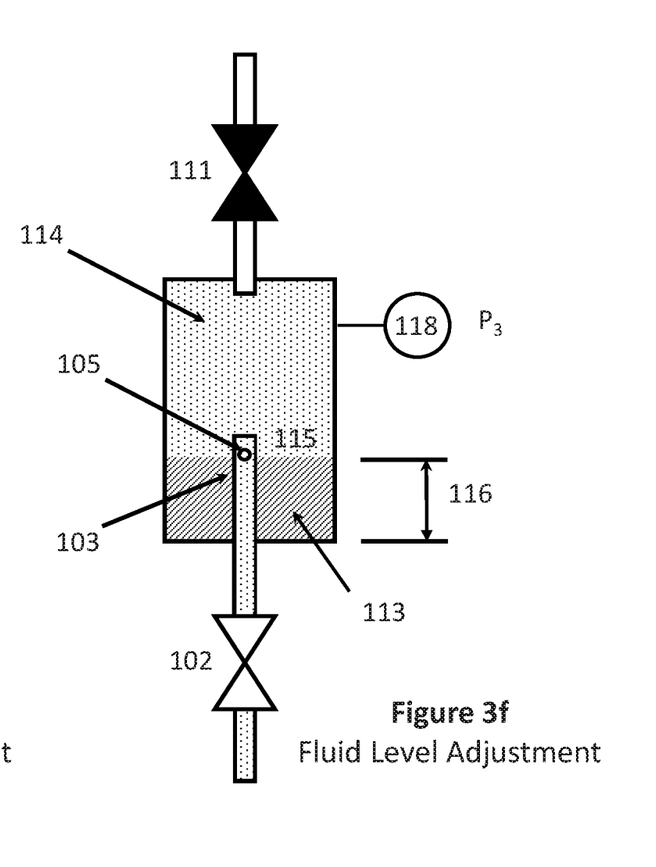
FIG. 3f is a schematic representation of the fluid level adjustment phase, in accordance with one embodiment of the present invention.
Figure 3G:
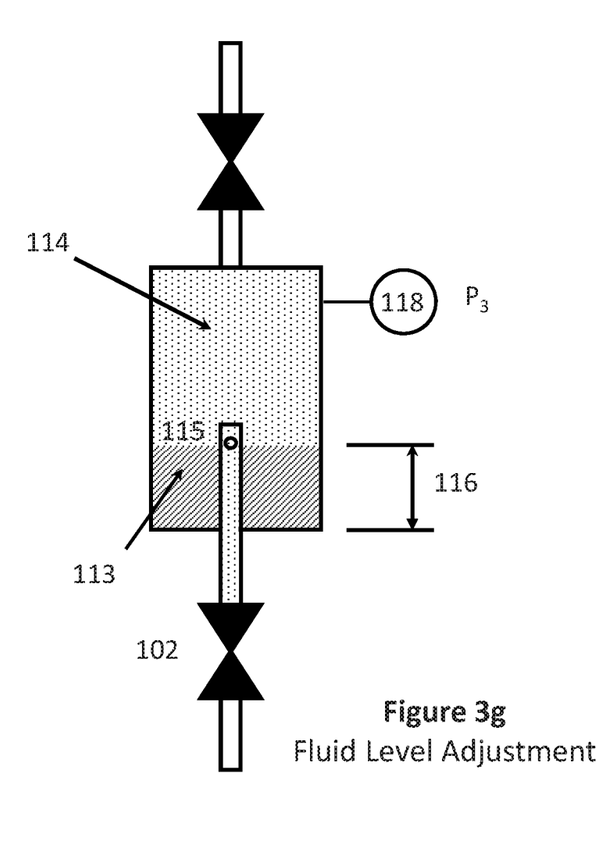
FIG. 3g is a schematic representation of the fluid level adjustment phase, in accordance with one embodiment of the present invention.

What may be referred to as the "fluid level adjustment phase" is indicated in FIGS. 3e-3g. As indicated in FIG. 3e, inlet valve 102 is now opened, preferably partially, to allow cryogenic liquid 113 to enter weir hole(s) 105, flow through weir tube 103 and inlet valve 102 and out cryogenic liquid inlet conduit to be vented or otherwise properly disposed of (not shown). As outlet valve 111 remains closed, the removal of cryogenic liquid 113 results in a lower pressure of P2 within inner volume 108, and the creation of a region of cryogenic vapor 114. P2 may be less than P1.

As indicated in FIG. 3f, cryogenic liquid 113 will cease to exit sampler vessel 107 once the free surface 115 of the cryogenic liquid is level 116 with the minimum fill point 106. If inlet valve 102 remains open beyond this time, only cryogenic vapor 114 will exit as the internal pressure of sampler vessel 107 continues to drop. At this time, a lower pressure P3 is present with inner volume 108, and the region of cryogenic vapor 114 is larger. P3 may be less than P2. As indicated in FIG. 3g, at this time inlet valve 102 is closed and the sampler vessel 107 is sealed. At this time, sample vessel is still at a very low temperature. Without some external refrigeration source, heat from the surrounding environment will enter sample vessel 107 and gradually the temperatures will reach equilibrium.

Figure 3H:
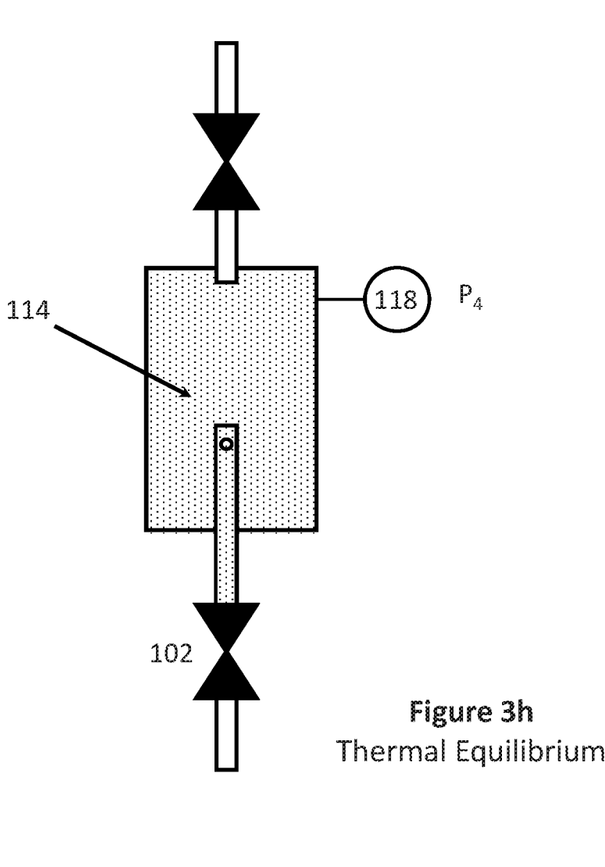
FIG. 3h is a schematic representation of the thermal equilibrium phase, in accordance with one embodiment of the present invention.

What may be referred to as the "thermal equilibrium phase" is indicated in FIG. 3h. As sampler vessel 107 reaches thermal equilibrium with the external environment, the temperature will rise to approximately ambient temperature, and the internal pressure P4 will simultaneously rise as all of the cryogenic liquid 113 becomes cryogenic vapor 114. P4 may be greater than P3. P4 may be greater than P1. Once this thermal equilibrium is approximately achieved, internal pressure P4 may be between 1000 psig and 1800 psig. Internal pressure P4 may be between 1100 psig and 1500 psig. Once sampler vessel 107 has reached the above equilibrium, it may be place in a carrying case if desired (not shown) and then may be transported to facility for testing.

Figure 4A:
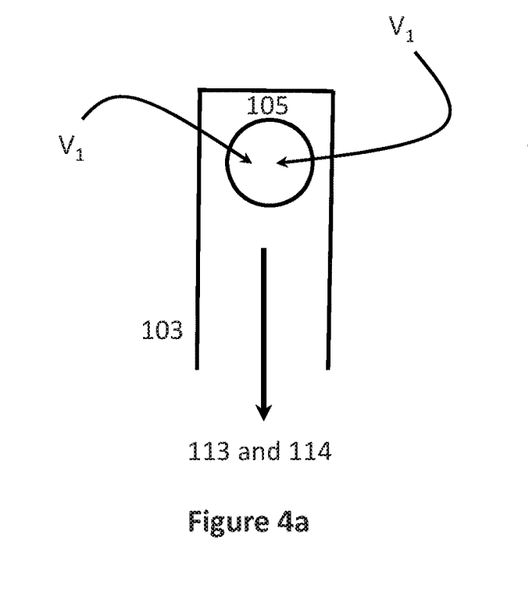
FIG. 4a is a schematic representation illustrating the fluid velocity entering weir holes of various sizes during the fluid level adjustment phase, in accordance with one embodiment of the present invention.

The addition of at least one weir hole 105 in weir tube 103 reduces the velocity of the fluid entering weir tube 103. During the initial stages of the fluid level adjustment phase, as indicated in FIG. 4a, there will be a region within sampler vessel 107 that experiences a transition of cryogenic liquid 113 into a vapor phase 114. During the initial stages, the weir hole will largely be immersed in liquid cryogen, but any turbulence that is experienced within sampler vessel 107 may cause a region of two phase (i.e. cryogenic liquid and cryogenic vapor) to form.

As indicated in FIGS. 3f and 3g, as the free surface 116 of the cryogenic liquid is at minimum fill point 106, weir hole 105, no additional liquid should exit sampler vessel 107, but the operator should only note cryogenic vapor 114 exiting. This should be the indication to close outlet valve 111. However, if weir hole 105 is improperly sized, entrained liquid may still exit sampler vessel 107, and an unknown amount of cryogenic liquid 113 may remain.

Figure 4B:
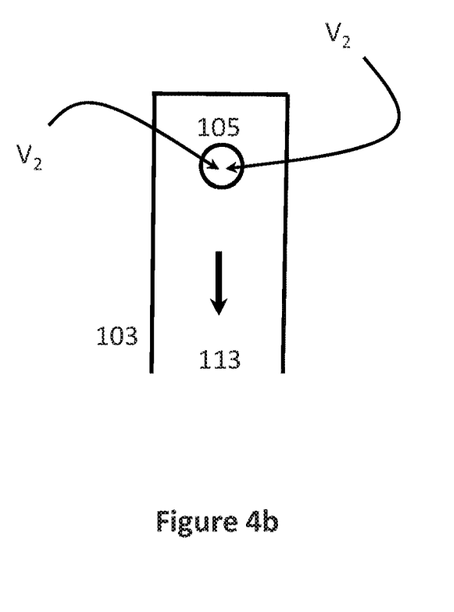
FIG. 4b is a schematic representation illustrating the fluid velocity entering weir holes of various sizes during the fluid level adjustment phase, in accordance with one embodiment of the present invention.
Figure 4C:
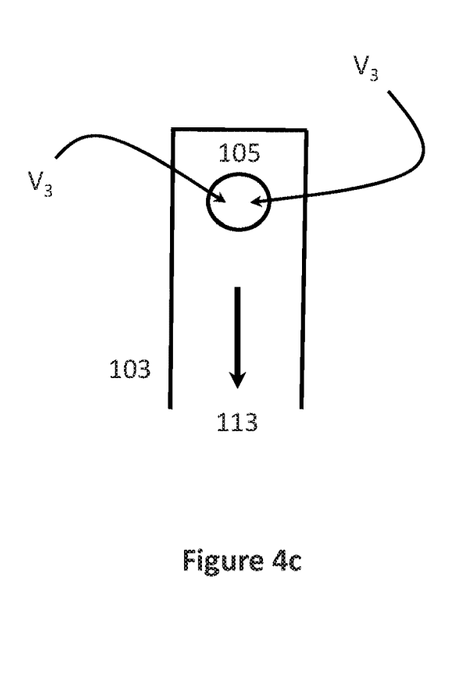
FIG. 4c is a schematic representation illustrating the fluid velocity entering weir holes of various sizes during the fluid level adjustment phase, in accordance with one embodiment of the present invention.

Such configurations are illustrated in FIGS. 4a-4c. In FIGS. 4a-4c the weir hole 105 is represented as being circular. However, this is merely representative and, as illustrated in FIGS. 2c and 2d, weir hole 105 may be rectangular. In FIG. 4a, weir hole 105 is too large and the velocity $V_1$ of the fluid entering from inner volume 105 is too high. This configuration allows for rapid filling and fluid level adjustment but also allows for a velocity that is sufficiently high as to allow two-phase fluid 115 to exit weir tube 103. In FIG. 5b, weir hole 105 is too small and the velocity $V_2$ of the fluid entering from inner volume 105 is too low. This configuration allows accurate fluid level adjustment and allows only cryogenic vapor 114 to enter weir tube 103 at the end of the fluid level adjustment period. However, this configuration requires a prohibitively long filling phase.

FIG. 5c illustrates a weir hole 105 that is appropriately sized. The velocity $V_3$ of the fluid entering from inner volume 105 is sufficiently high to allow for a reasonable filling and fluid level adjustment time. But this configuration does not have sufficiently high velocity to allow excess entrained liquid to enter weir tube 105 at the end of the fluid level adjustment period, only allowing cryogenic vapor 114.

Figure 5:
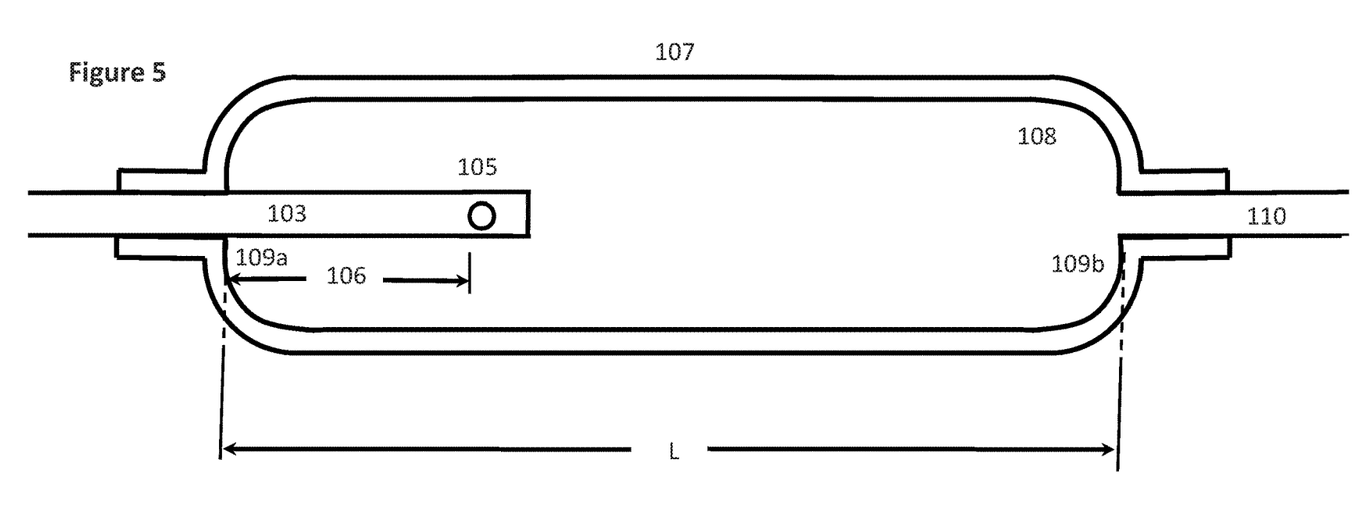
FIG. 5 is a schematic representation illustrating the useful internal length of the sampler vessel.

The distance 117 of minimum fill point 106 from the inner wall 109 of sampler vessel 107 depends on the specific requirements of the particular cryogenic liquid sampler 100. As indicated in FIG. 5, a useful internal length L of sampler vessel 107, may be defined as the distance between the inner wall 109a at one end, and the inner wall 109b at the opposite end of sampler vessel 107. This useful internal length L will depend on the actual shape of the particular sampler vessel, but will generally be the length of the internal volume 108, which will be filled with cryogenic liquid 113 during the filling phase of the method. In some embodiments distance 117 may be between about ¼ and about ½ of L.

The diameter $D_{wh}$ of a circular weir hole 105 depends on the specific requirements of the particular cryogenic liquid sampler 100. If $D_{wt}$ is the nominal outside diameter of weir tube 103, then in some embodiments $D_{wh}$ may be between about ¼ and about ½ of $D_{wt}$.

The height $H_{wh}$ and/or $W_{wh}$ width of a rectangular weir hole 105 depends on the specific requirements of the particular cryogenic liquid sampler 100. If $D_{wt}$ is the nominal outside diameter of weir tube 103, then in some embodiments $W_{wh}$ may be between about ¼ and about ½ of $D_{wt}$. In some embodiments $W_{wh}$ may be between about ⅓ and about ¾ of $D_{wt}$. In some embodiments $H_{wh}$ may be between about ⅓ and about ¾ of $H_{wt}$.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of taking a cryogenic liquid sample, with a cryogenic liquid sampler comprising:
   a sampler vessel comprising an inner volume, and an inner wall,
   a cryogenic liquid inlet conduit in fluid connection with an inlet valve,
   a weir tube in fluid connection with the inlet valve,
      wherein the weir tube has a top plug and at least one weir hole through a circumferential surface of the weir tube,
      wherein the weir tube extends into the inner volume,
      wherein a first cryogenic liquid level is the distance along the weir tube between the inner wall and the at least one weir hole,
   a cryogenic liquid outlet conduit in fluid connection with the inner volume and in fluid connection with an outlet valve, and a purge tube in fluid connection with the outlet valve, the method comprising;
a) closing both the inlet valve and the outlet valve,
b) connecting a cryogenic liquid source to the cryogenic liquid inlet conduit, and introducing cryogenic liquid into the cryogenic liquid inlet conduit;
c) opening both the inlet valve and outlet valve, thereby introducing cryogenic liquid into the sampler vessel inner volume, wherein the cryogenic liquid has a free surface;
d) closing both the inlet valve and the outlet valve after cryogenic liquid flows from the purge tube;
e) disconnecting the cryogenic liquid source from the cryogenic liquid inlet conduit;
f) opening the inlet valve, thereby allowing cryogenic liquid to flow from the cryogenic liquid inlet conduit; and
g) closing the inlet valve after the free surface in the sampler vessel inner volume drops below the top of the first cryogenic liquid level, and the cryogenic liquid flow stops.

2. The method of claim 1, wherein the sampler vessel comprises a wall temperature, and further comprising:
h) allowing the wall temperature to reach approximately ambient temperature.

3. The method of claim 2, the sampler vessel further comprising an internal pressure, wherein during step h) the internal pressure rises to a pressure between about 1000 psig and about 1800 psig.

4. The method of claim 3, wherein the internal pressure rises to a pressure between about 1100 psig and about 1500 psig.

5. The method of claim 1, wherein the weir tube has an outside diameter of $D_{wt}$, wherein the at least one weir hole has a generally circular shape and a diameter of $D_{wh}$, and wherein $D_{wh}/D_{wt}$ is between about ¼ and about ½.

6. The method of claim 1, wherein the weir tube has an outside diameter of $D_{wt}$, wherein the at least one weir hole has a generally rectangular shape, a height of $H_{wh}$, a width of $W_{wh}$ and wherein $H_{wh}/D_{wt}$ is between about ⅓ and about ¾, and wherein $W_{wh}/D_{wt}$ is between about ⅓ and about ¾.

7. The method of claim 1, wherein the weir tube extends a predetermined distance into the inner volume and the predetermined distance is between about ¼ and ½ of a useful internal length of the sampler vessel.

8. The method of claim 1, wherein during step d) the sampler vessel has an internal pressure of P1, wherein during step f) the sampler vessel has an internal pressure of P2, and wherein P2<P1.

9. The method of claim 2, wherein during step d) the sampler vessel has an internal pressure of P1, wherein during step h) the sampler vessel has an internal pressure of P4, and wherein P4<P1.

10. A method for sampling a cryogenic liquid while maintaining the constituent composition, with a cryogenic liquid sampler comprising:
a sampler vessel comprising an inner volume and an inner wall,
a cryogenic liquid inlet conduit in fluid connection with an inlet valve,
a weir tube in fluid connection with the inlet valve,
wherein the weir tube has a top plug and at least one weir hole through a circumferential surface of the weir tube,
wherein the weir tube extends a predetermined distance into the inner volume,
a cryogenic liquid outlet conduit in fluid connection with the inner volume and in fluid connection with an outlet valve, and
a purge tube in fluid connection with the outlet valve,
a) filling the cryogenic liquid sampler with a cryogenic liquid with a constituent composition,
b) removing a stream of cryogenic liquid from the sampler through the weir tube, thereby creating a lower pressure region of vapor above the cryogenic liquid with the constituent composition, and
c) sealing the cryogenic liquid sampler once the stream of cryogenic liquid stops, thereby retaining a residual portion of cryogenic liquid with the constituent composition.

11. The method of claim 10, wherein the cryogenic liquid sampler comprises a wall temperature, and further comprising:
d) allowing the wall temperature to reach approximately ambient temperature.

12. The method of claim 11, the cryogenic liquid sampler further comprising an internal pressure, wherein during step d) the internal pressure rises to a pressure between about 1000 psig and about 1800 psig.

13. The method of claim 12, wherein the internal pressure rises to a pressure between about 1100 psig and about 1500 psig.

14. The method of claim 10, wherein the weir tube has an outside diameter of $D_{wt}$, wherein the at least one weir hole has a generally circular shape and a diameter of $D_{wh}$, and wherein $D_{wh}/D_{wt}$ is between about ¼ and about ½.

15. The method of claim 10, wherein the weir tube has an outside diameter of $D_{wt}$, wherein the at least one weir hole has a generally rectangular shape, a height of $H_{wh}$, a width of $W_{wh}$ and wherein $H_{wh}/D_{wt}$ is between about ⅓ and about ¾, and wherein $W_{wh}/D_{wt}$ is between about ⅓ and about ¾.

16. The method of claim 10, wherein the predetermined distance is between about ¼ and ½ of a useful internal length of the sampler vessel.

17. The method of claim 10, wherein during step d) the sampler vessel has an internal pressure of P1, wherein during step f) the sampler vessel has an internal pressure of P2, and wherein P2<P1.

18. The method of claim 11, wherein during step d) the sampler vessel has an internal pressure of P1, wherein during step h) the sampler vessel has an internal pressure of P4, and wherein P4<P1.

* * * * *